United States Patent [19]
Chu et al.

[11] Patent Number: 6,044,981
[45] Date of Patent: Apr. 4, 2000

[54] MICROFABRICATED FILTER WITH SPECIALLY CONSTRUCTED CHANNEL WALLS, AND CONTAINMENT WELL AND CAPSULE CONSTRUCTED WITH SUCH FILTERS

[75] Inventors: Wen-Hwa Chu, Albany; Mauro Ferrari, Lafayette, both of Calif.

[73] Assignee: The Regents of the University of California, Oakland, Calif.

[21] Appl. No.: 09/139,883

[22] Filed: Aug. 25, 1998

Related U.S. Application Data

[60] Division of application No. 08/663,644, Jun. 14, 1996, Pat. No. 5,798,042, which is a continuation-in-part of application No. 08/482,237, Jun. 7, 1995, Pat. No. 5,770,076, which is a continuation-in-part of application No. 08/254,330, Jun. 6, 1994, Pat. No. 5,893,974, which is a continuation-in-part of application No. 08/207,457, Mar. 7, 1994, Pat. No. 5,651,900, and a continuation-in-part of application No. 08/207,459, Mar. 7, 1994, Pat. No. 5,660,680.

[51] Int. Cl.[7] ............................ B01D 69/10; B01D 69/06; C23F 1/00; A61K 9/22
[52] U.S. Cl. ......................... 210/490; 210/321.84; 216/2; 216/56; 424/424; 604/891.1
[58] Field of Search ..................... 210/321.83, 321.84, 210/483, 484, 490, 500.22, 500.25, 500.26; 216/2, 56; 424/422–424, 451; 604/890.1, 891.1, 892.1; 623/11, 12; 422/100, 101

[56] References Cited

U.S. PATENT DOCUMENTS

| | | | |
|---|---|---|---|
| 2,226,381 | 12/1940 | Norris | 216/56 |
| 2,226,383 | 12/1940 | Norris | 216/56 |
| 2,226,384 | 12/1940 | Norris | 216/56 |

(List continued on next page.)

FOREIGN PATENT DOCUMENTS

| | | | |
|---|---|---|---|
| 1-138110 | 5/1989 | Japan. | |
| 1680270 | 9/1991 | U.S.S.R. | 210/506 |
| 563302 | 8/1944 | United Kingdom | 216/56 |
| WO A 89/08489 | 9/1989 | WIPO. | |
| WO A 92/15408 | 9/1992 | WIPO. | |
| WO 93/11862 | 6/1993 | WIPO. | |

OTHER PUBLICATIONS

G. Kittilsland et al., "A Sub–Micron Particle Filter in Silicon," *Sensors and Actuators*, A21–A23, (1990), pp. 904–907.

W. Lang et al., "Application of Porous Silicon as a Sacrificial Layer," *7th International Conference on Solid–State Sensors and Actuators Digest of Technical Papers*, Jun. 7–10, 1993, pp. 202–205.

*Websters Third New International Dictionary*, Copyright 1986 by Merriam–Webster, Inc., p. 811.

(List continued on next page.)

*Primary Examiner*—Joseph W. Drodge
*Attorney, Agent, or Firm*—Fish & Richardson P.C.

[57] ABSTRACT

Microfabricated filters utilizing a bulk substrate structure and a thin film structure and a method for constructing such filters. The pores of the filters are defined by spaces between the bulk substrate structure and the thin film structure and are of substantially uniform width, length and distribution. The width of the pores is defined by the thickness of a sacrificial layer and therefore may be smaller than the limit of resolution obtainable with photolithography. The filters provide enhanced mechanical strength, chemical inertness, biological compatibility, and throughput. The filters are constructed using relatively simple fabrication techniques. Also, microfabricated containment wells and capsules constructed with such filters for the immunological isolation of cell transplants and a method for constructing such containment wells and capsules. The pores of the wells and capsules are large enough to let a desired biologically-active molecular product through, while blocking the passage of all larger immunological molecules. The containment wells and capsules provide enhanced biological compatibility and useful life.

24 Claims, 14 Drawing Sheets

U.S. PATENT DOCUMENTS

| | | | |
|---|---|---|---|
| 2,246,380 | 6/1941 | Norris | 216/56 |
| 3,329,541 | 7/1967 | Mears | 216/56 |
| 3,502,455 | 3/1970 | Gardner | 65/31 |
| 3,556,945 | 1/1971 | Messing . | |
| 3,600,147 | 8/1971 | McKinnis et al. | 65/31 |
| 3,791,987 | 2/1974 | Fanger | 264/4 |
| 3,841,971 | 10/1974 | Messing . | |
| 3,845,770 | 11/1974 | Theeuwes et al. | 128/260 |
| 3,936,329 | 2/1976 | Kendall et al. | 437/974 |
| 3,962,052 | 6/1976 | Abbas et al. | 204/129.3 |
| 4,063,271 | 12/1977 | Bean et al. | 357/49 |
| 4,077,885 | 3/1978 | Van Heuven et al. | 210/193 |
| 4,078,971 | 3/1978 | Arkles et al. . | |
| 4,177,228 | 12/1979 | Prölss | 264/24 |
| 4,217,898 | 8/1980 | Theeuwes | 128/260 |
| 4,307,507 | 12/1981 | Gray et al. | 437/974 |
| 4,369,565 | 1/1983 | Muramatsu | 29/580 |
| 4,409,331 | 10/1983 | Lim | 435/178 |
| 4,455,143 | 6/1984 | Theeuwes et al. | 604/890.1 |
| 4,473,476 | 9/1984 | McMillan et al. | 210/653 |
| 4,626,244 | 12/1986 | Reinicke | 604/891.1 |
| 4,673,566 | 6/1987 | Goosen et al. | 424/19 |
| 4,689,150 | 8/1987 | Abe et al. | 210/490 |
| 4,698,900 | 10/1987 | Esquivel | 457/52 |
| 4,743,545 | 5/1988 | Torobin | 435/41 |
| 4,793,825 | 12/1988 | Benjamin et al. | 604/891.1 |
| 4,797,175 | 1/1989 | Elion et al. | 216/56 |
| 4,797,211 | 1/1989 | Ehrfeld et al. | 210/500.25 |
| 4,814,083 | 3/1989 | Ford et al. | 210/500.25 |
| 4,841,228 | 6/1989 | Zentner et al. | 424/456 |
| 4,851,228 | 7/1989 | Zentner et al. | 424/456 |
| 4,853,001 | 8/1989 | Hammel | 65/31 |
| 4,874,484 | 10/1989 | Foell et al. | 204/129.3 |
| 4,937,209 | 6/1990 | Jones et al. | 501/80 |
| 4,981,590 | 1/1991 | Van 'T Veen et al. | 210/490 |
| 5,126,810 | 6/1992 | Gotou | 357/23.6 |
| 5,131,978 | 7/1992 | O'Neill | 156/653 |
| 5,156,623 | 10/1992 | Hakamatsuka et al. | 604/891.1 |
| 5,160,617 | 11/1992 | Huis Int'l Veld et al. | 210/490 |
| 5,183,607 | 2/1993 | Beall et al. | 264/41 |
| 5,200,334 | 4/1993 | Dunn et al. | 501/12 |
| 5,225,123 | 7/1993 | Torobin | 264/43 |
| 5,230,693 | 7/1993 | Williams et al. | 600/36 |
| 5,234,594 | 8/1993 | Tonucci et al. | 210/500.26 |
| 5,238,613 | 8/1993 | Anderson | 264/22 |
| 5,262,021 | 11/1993 | Lehman et al. | 204/129.55 |
| 5,271,801 | 12/1993 | Valette | 156/653 |
| 5,275,766 | 1/1994 | Gadkaree et al. | 65/31 |
| 5,304,487 | 4/1994 | Wilding et al. | 435/291 |
| 5,314,471 | 5/1994 | Brauker et al. | 604/891.1 |
| 5,376,347 | 12/1994 | Ipponmatsu et al. | 423/338 |
| 5,431,921 | 7/1995 | Thombre | 424/424 |
| 5,453,278 | 9/1995 | Chan et al. | 424/422 |
| 5,543,046 | 8/1996 | Van Rijn | 210/500.26 |
| 5,585,011 | 12/1996 | Saaski et al. | 216/2 |
| 5,585,069 | 12/1996 | Zanzuechi et al. | 422/100 |
| 5,603,953 | 2/1997 | Herbig et al. | 424/451 |
| 5,629,008 | 5/1997 | Lee | 604/890.1 |
| 5,651,900 | 7/1997 | Keller et al. | 240/500.26 |
| 5,653,406 | 8/1997 | Clarke et al. | 623/11 |
| 5,660,680 | 8/1997 | Keller | 216/2 |
| 5,660,728 | 8/1997 | Saaski et al. | 210/321.84 |
| 5,807,406 | 9/1998 | Brauker et al. | 623/11 |
| 5,919,364 | 7/1999 | Lebouitz et al. | 210/500.26 |
| 5,938,927 | 8/1999 | Tu et al. | 210/500.26 |
| 5,948,255 | 9/1999 | Keller et al. | 210/500.26 |

OTHER PUBLICATIONS

Giermund Kittilsland et al., "A Sub–micron Particle Filter in Silicon," *Sensors and Actuators*, A21–A23, 1990, pp. 904–907.

J.P. Brody et al., "A Planar Microfabricated Fluid Filter," *8th International Conference on Solid–State Sensors and Actuators,* Jun. 25–29, 1995, pp. 779–82.

D. H. Pearson et al., "Nanochannel Glass Replica Membranes," *Science,* vol. 270, Oct. 6, 1995, pp. 68–69.

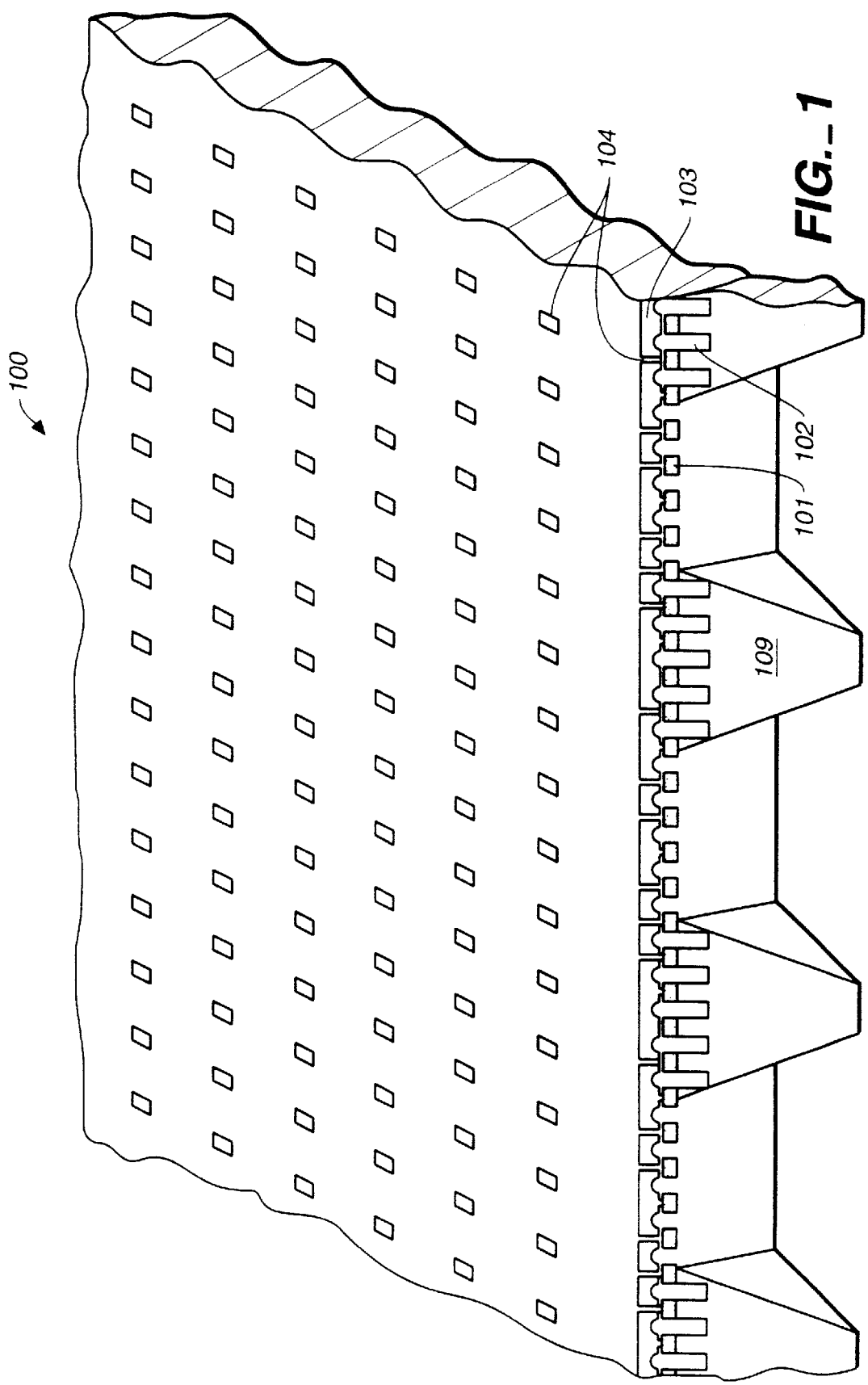
FIG._1

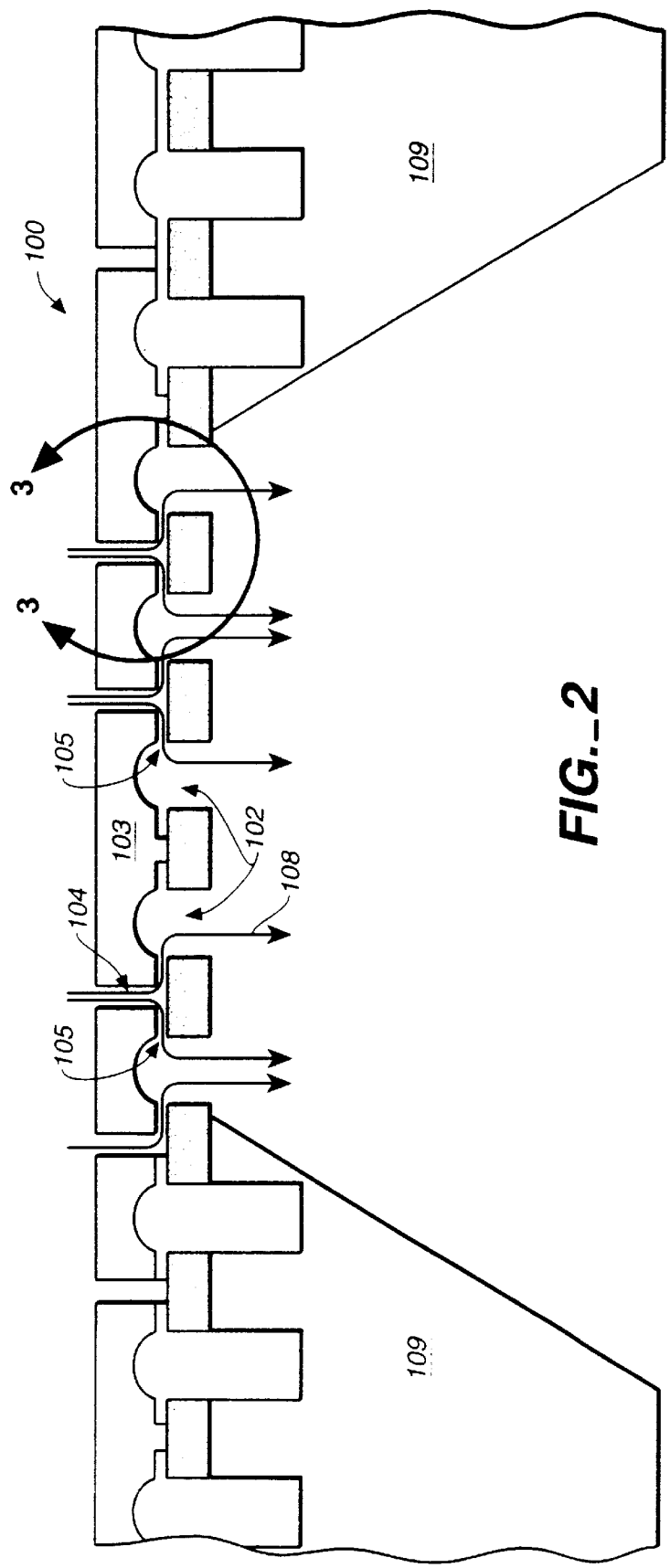
FIG._2

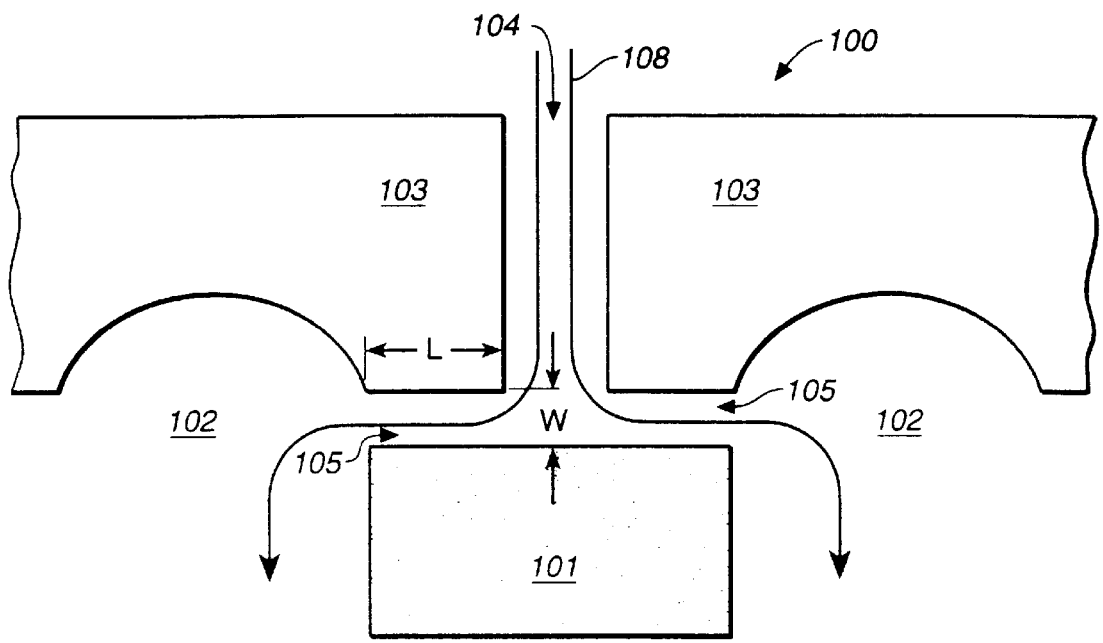
FIG._3
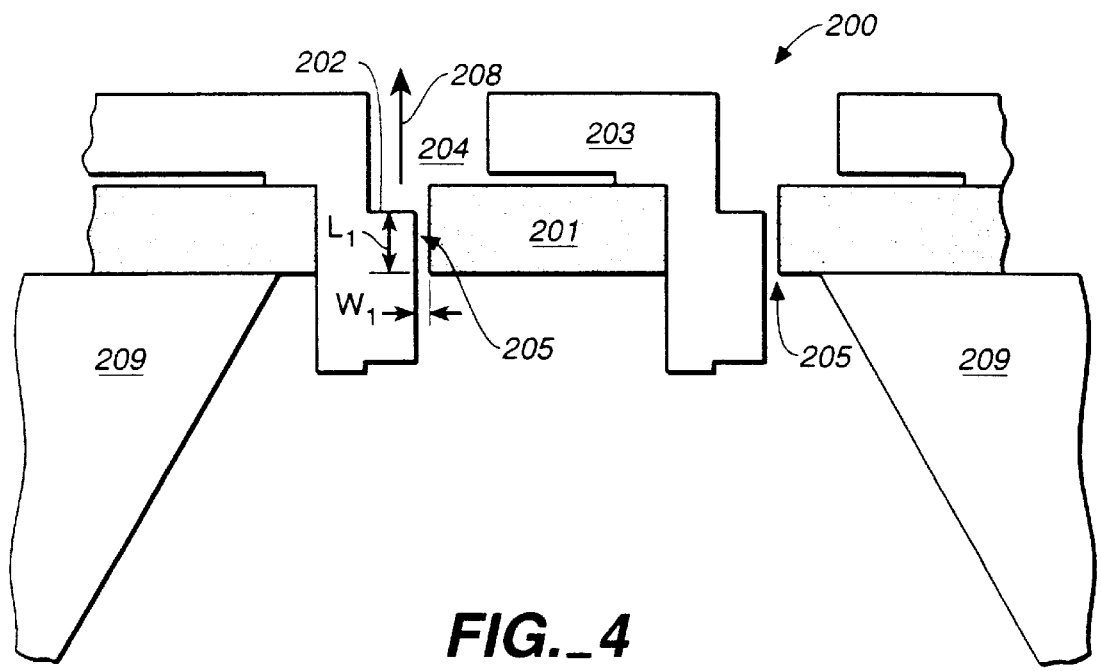
FIG._4

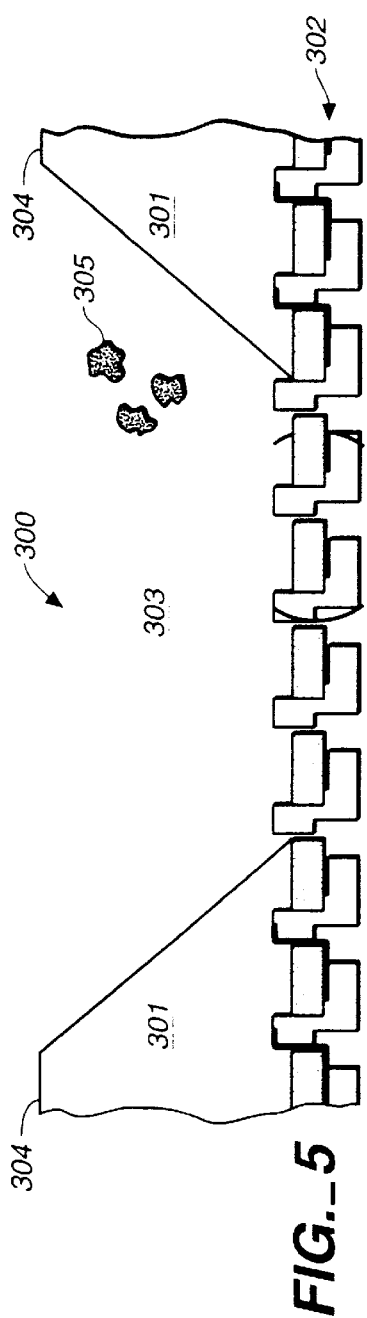
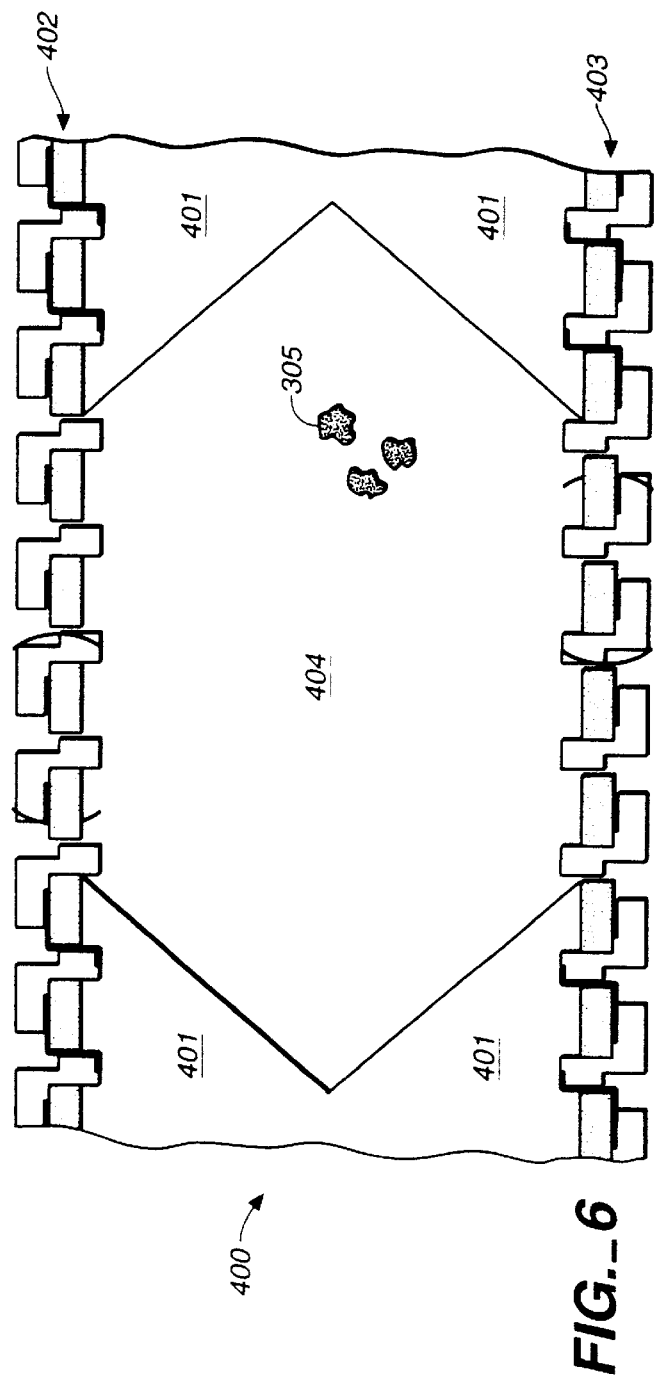
FIG._5
FIG._6

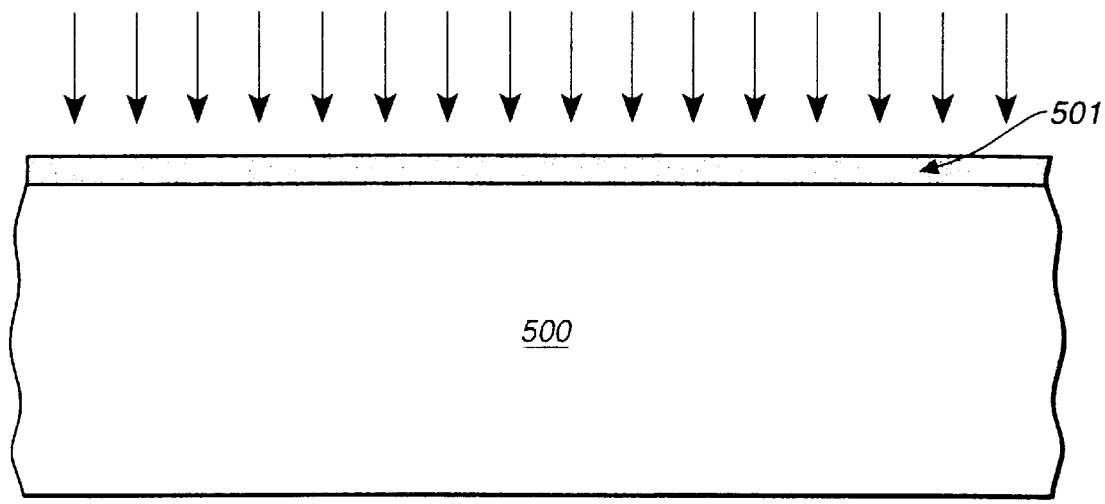
FIG._7
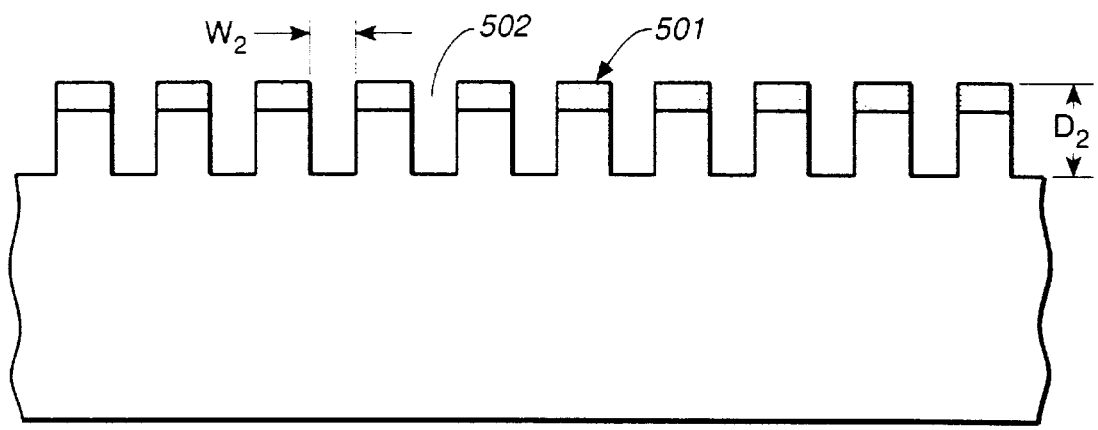
FIG._8
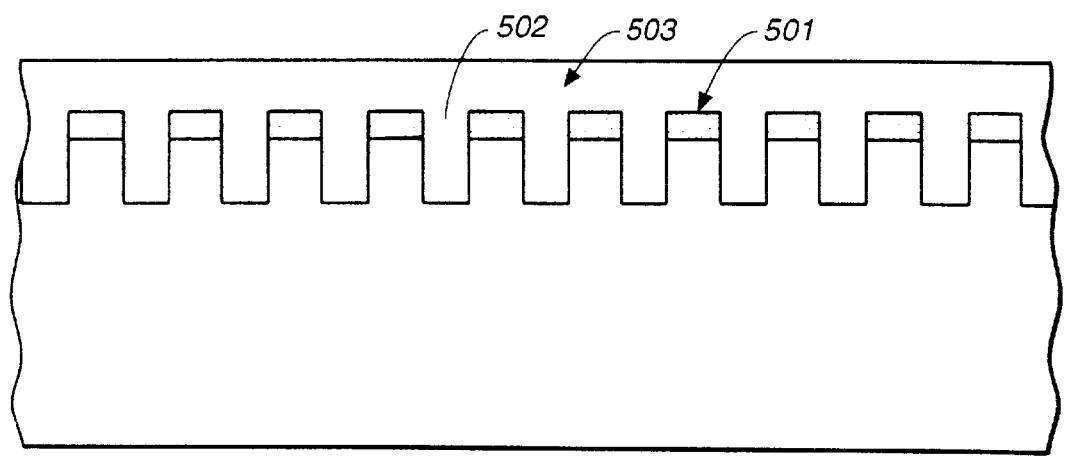
FIG._9

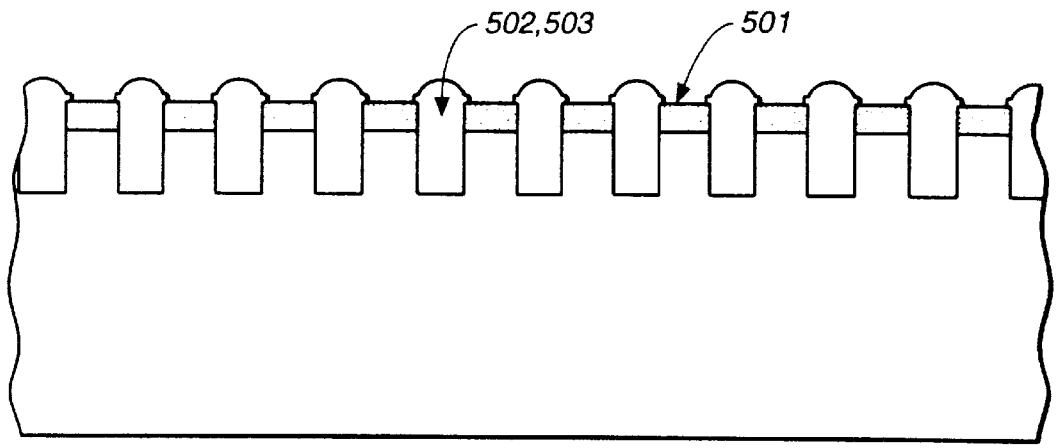
FIG._10
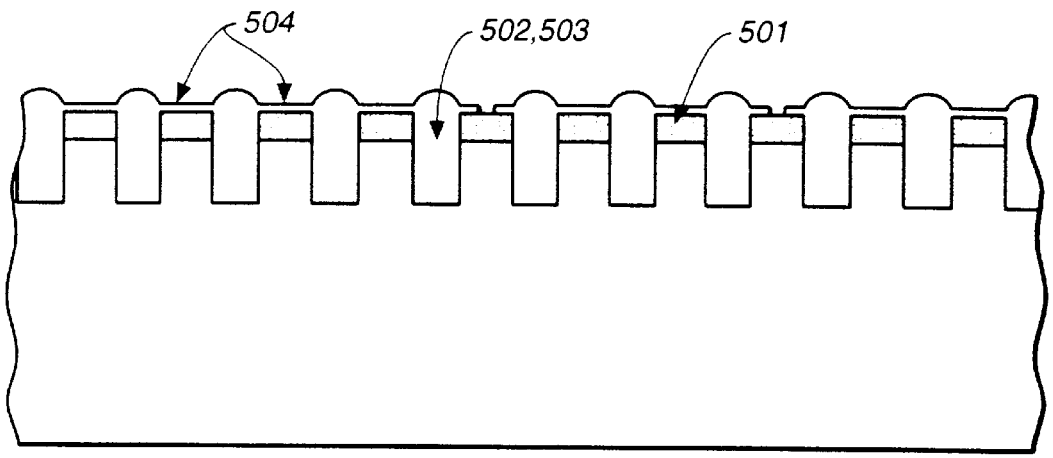
FIG._11
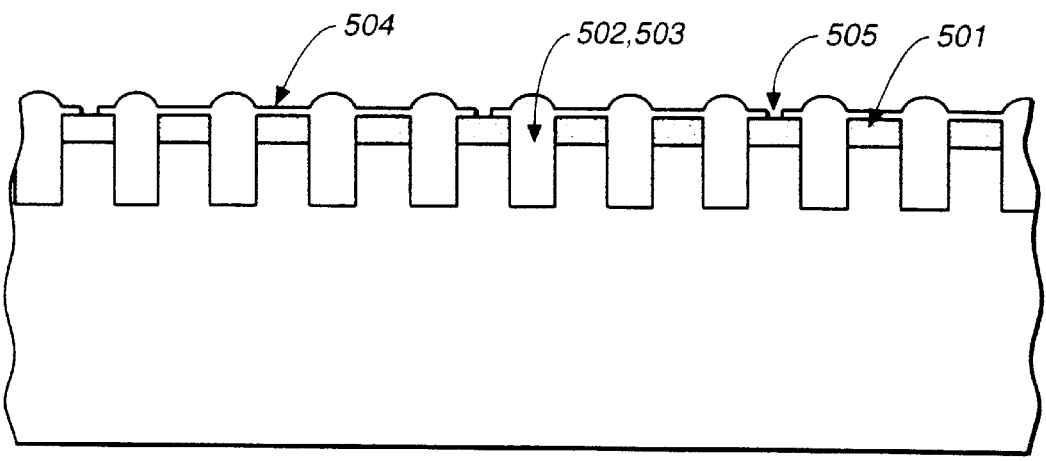
FIG._12

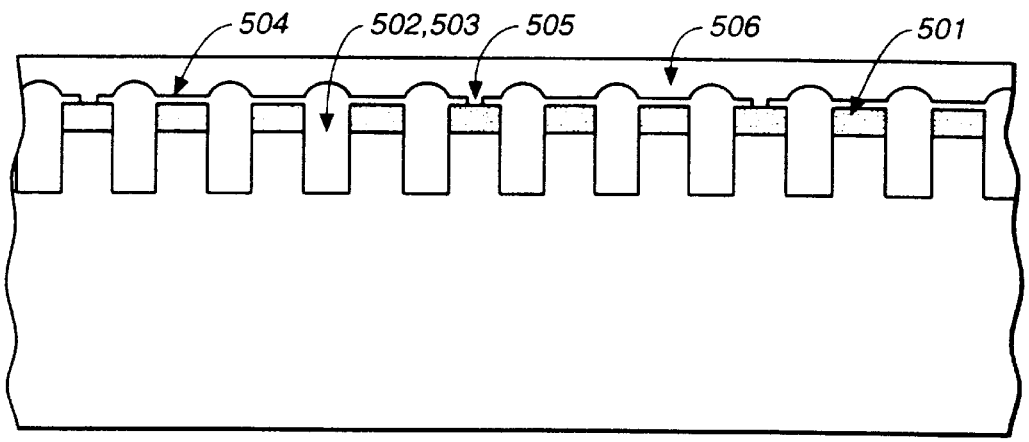
FIG._13
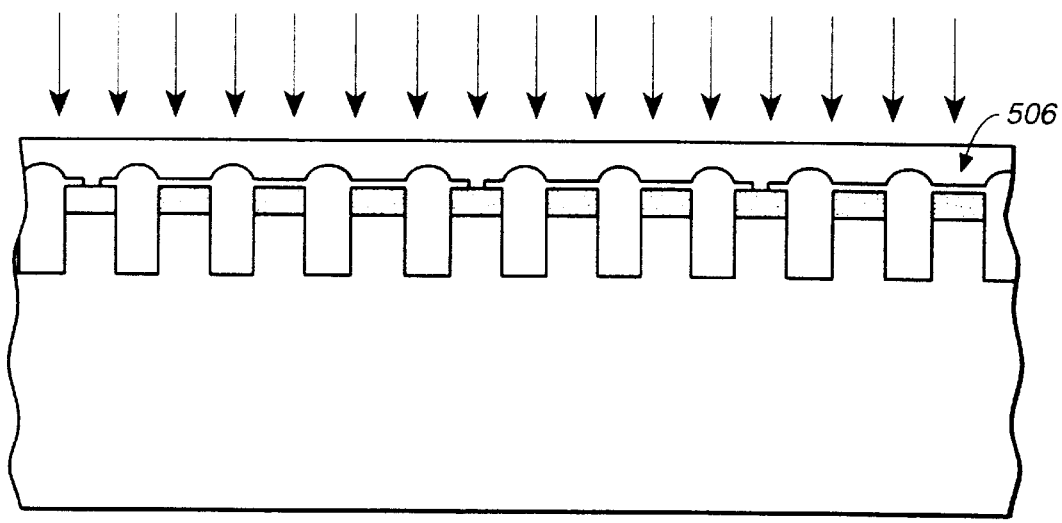
FIG._14
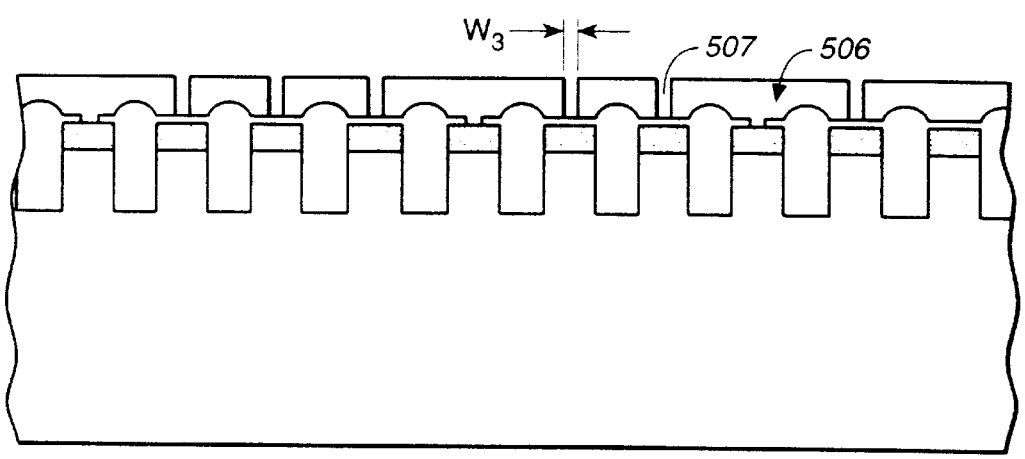
FIG._15

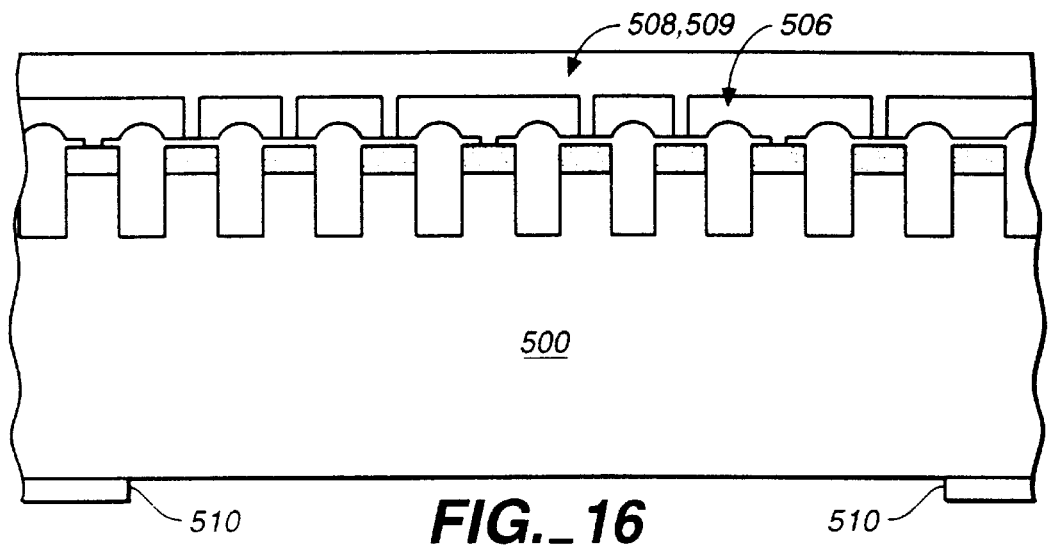
FIG._16
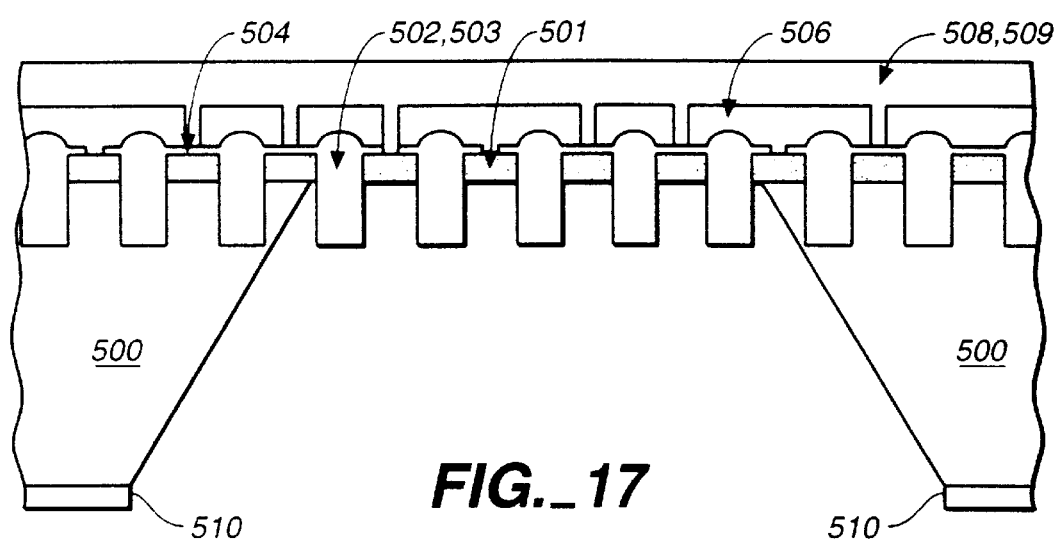
FIG._17
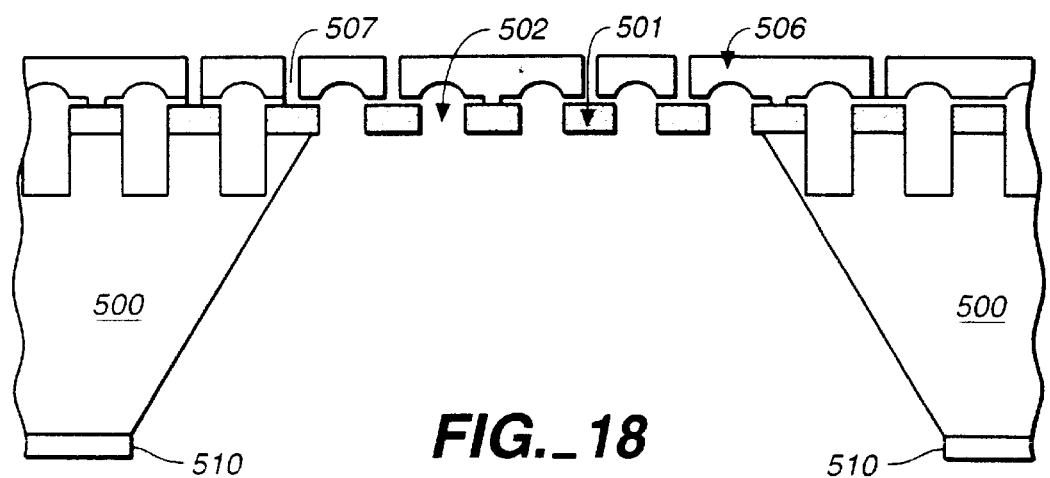
FIG._18

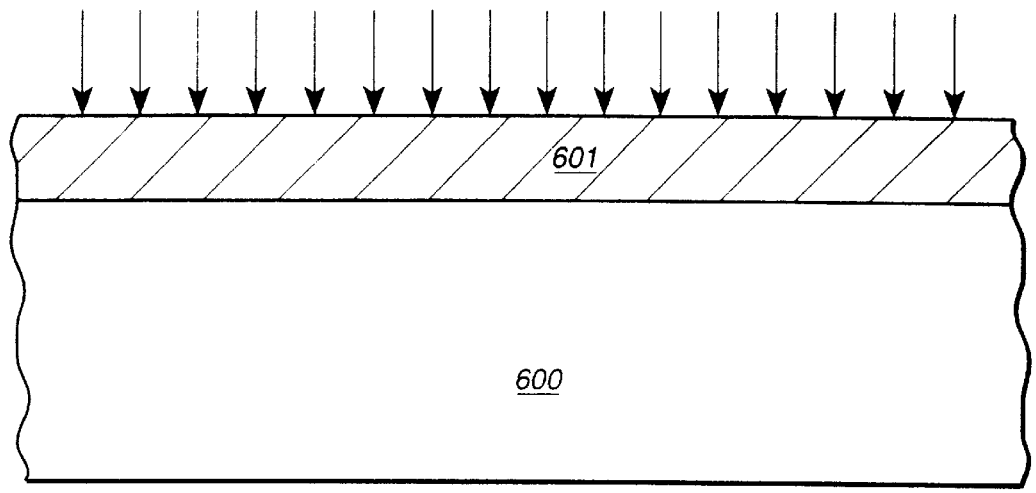
FIG._19
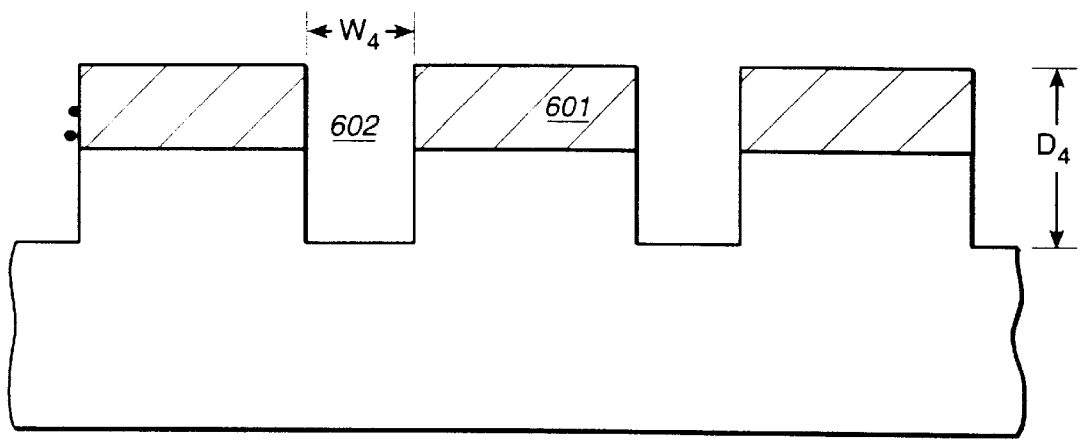
FIG._20

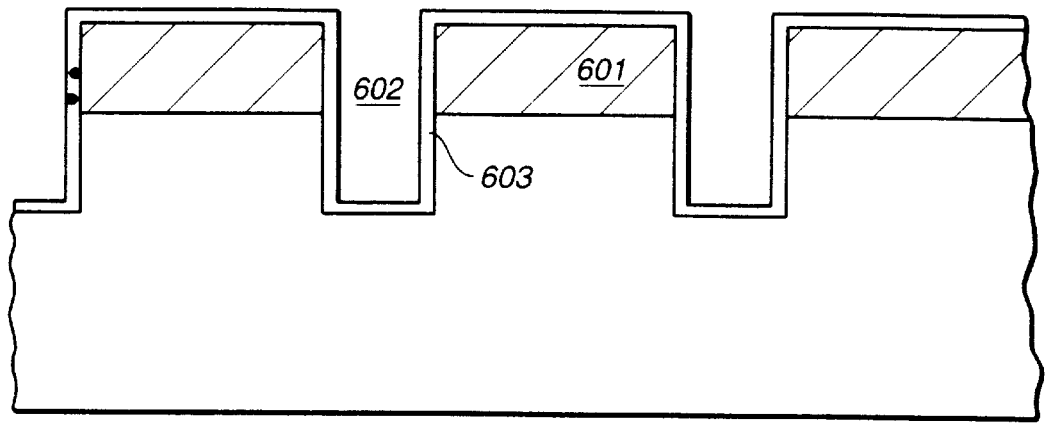
FIG._21
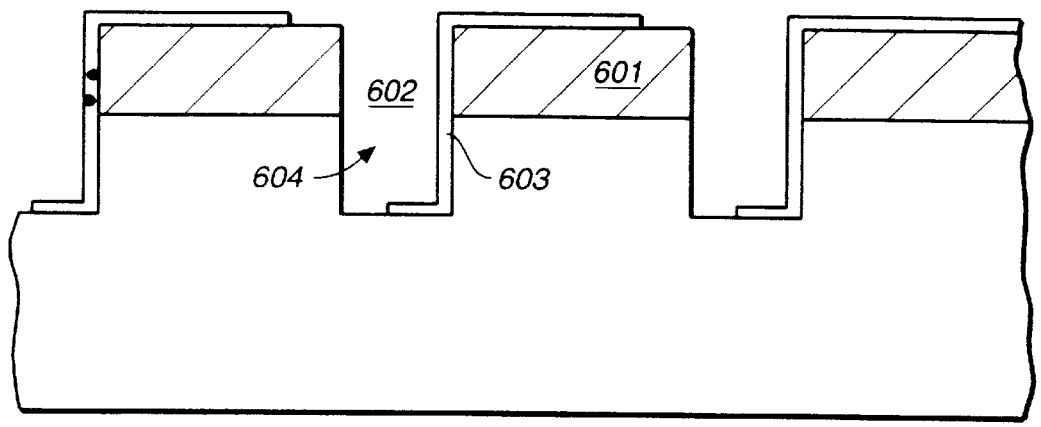
FIG._22
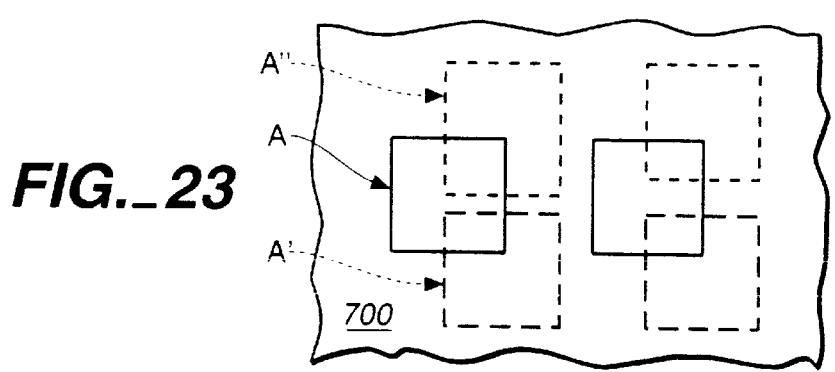
FIG._23

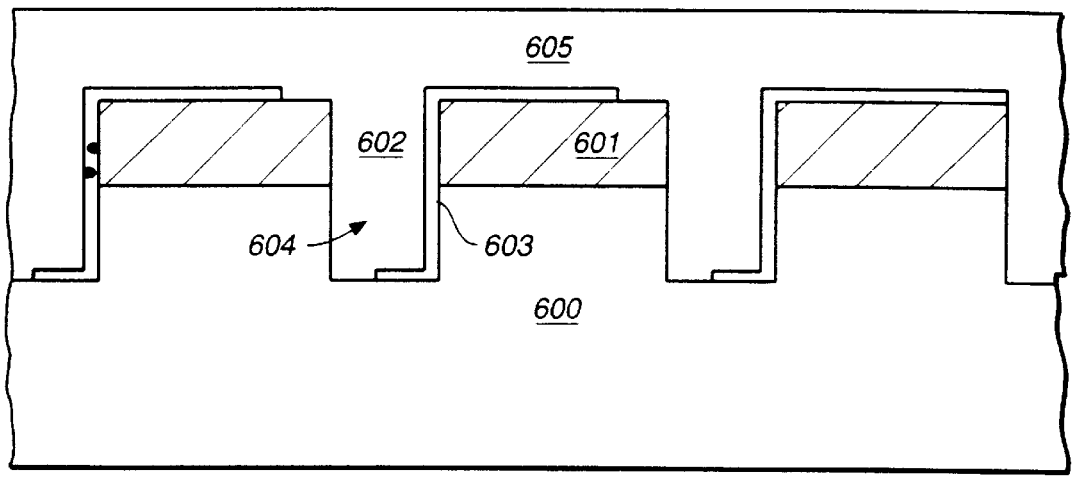
FIG._24
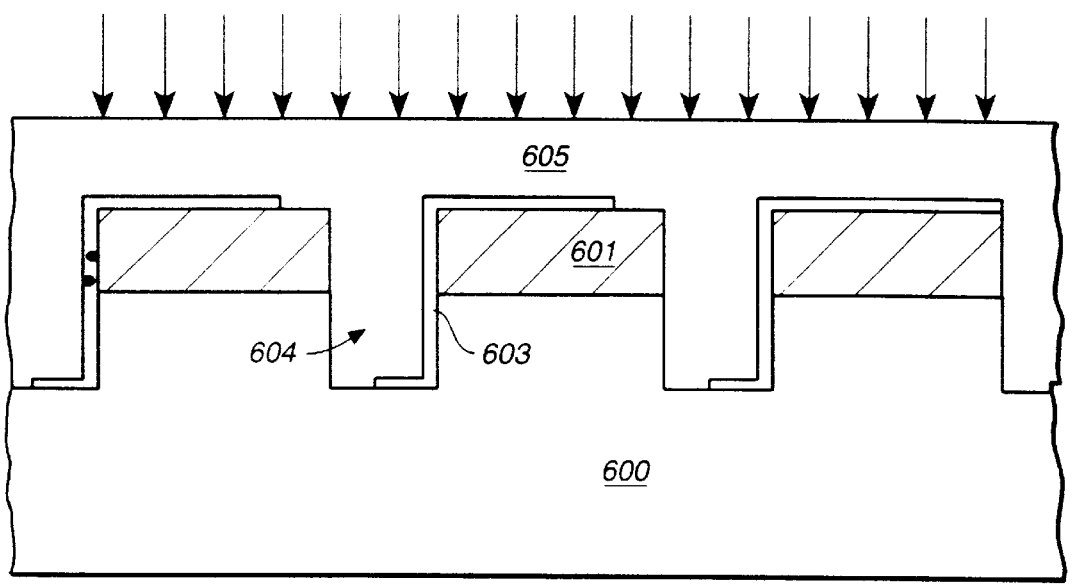
FIG._25

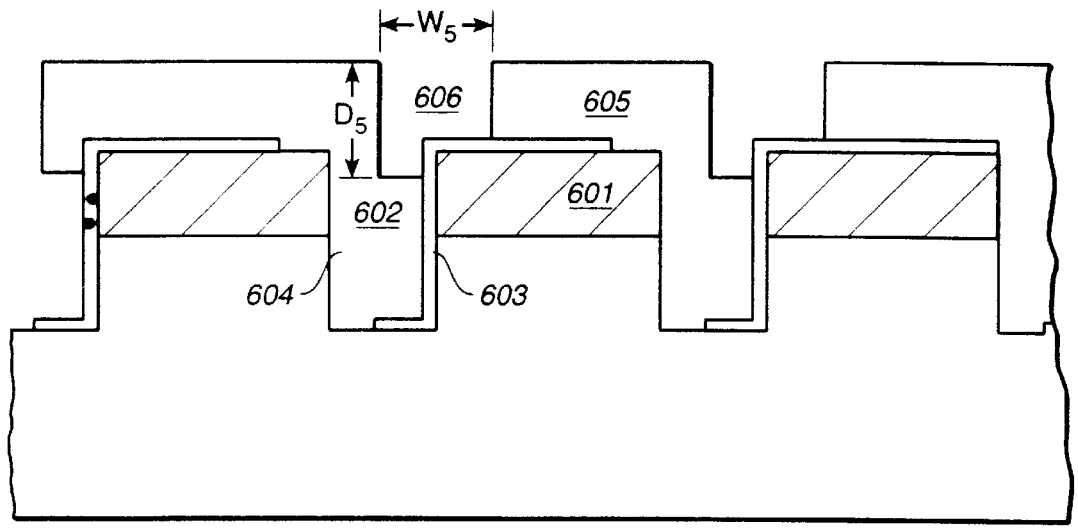
FIG._26
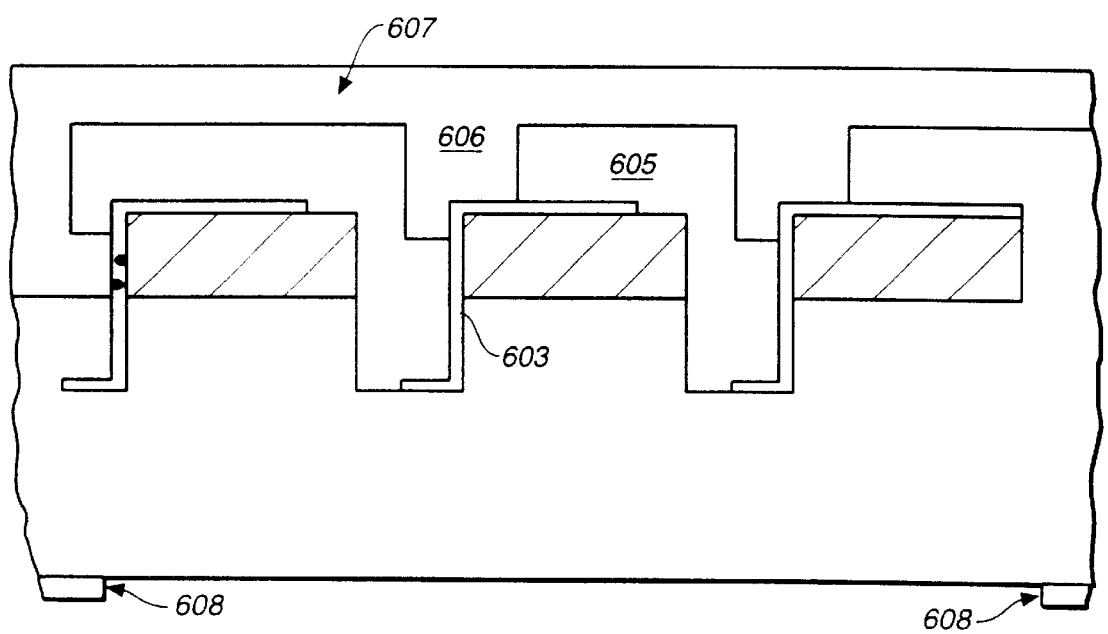
FIG._27

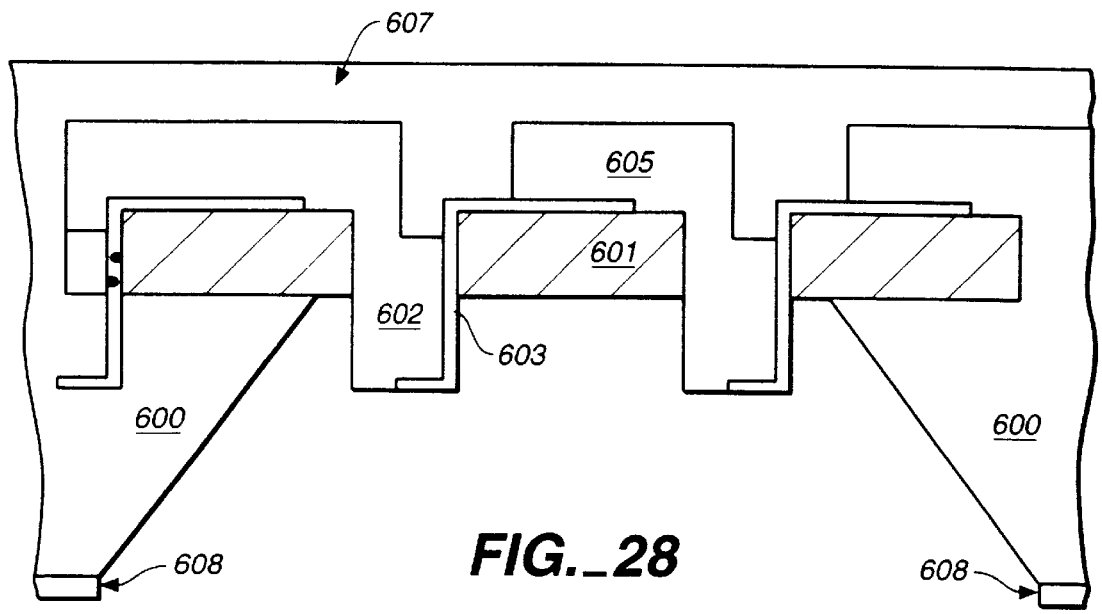
FIG._28
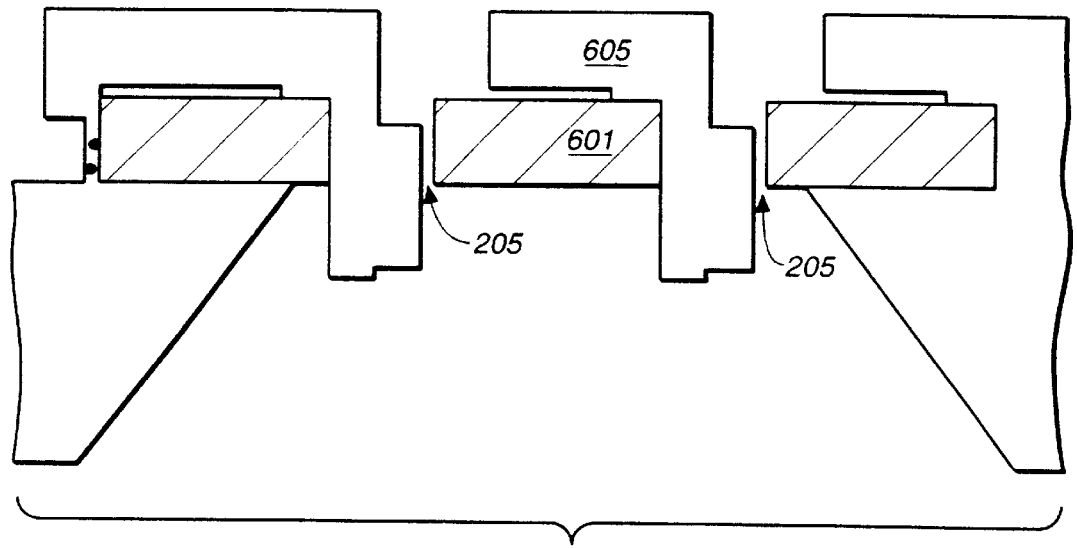
FIG._29

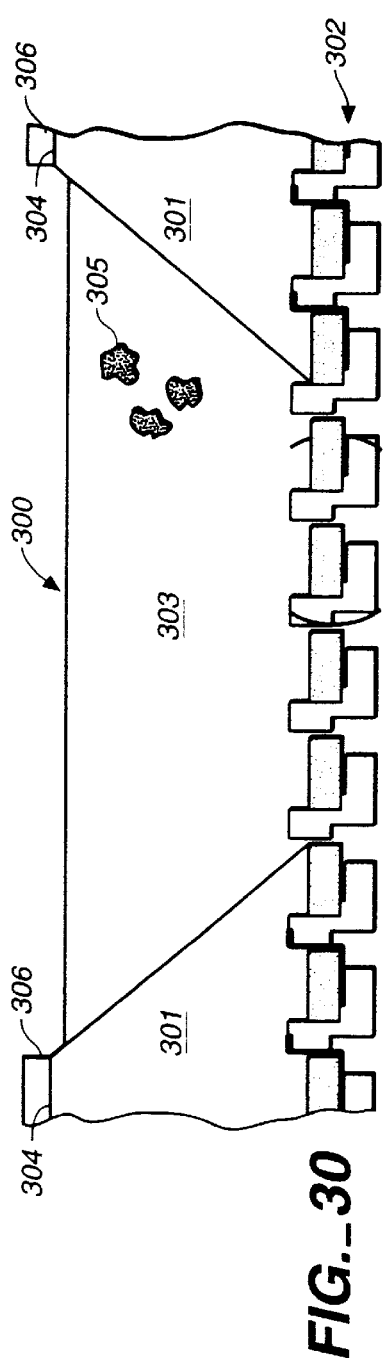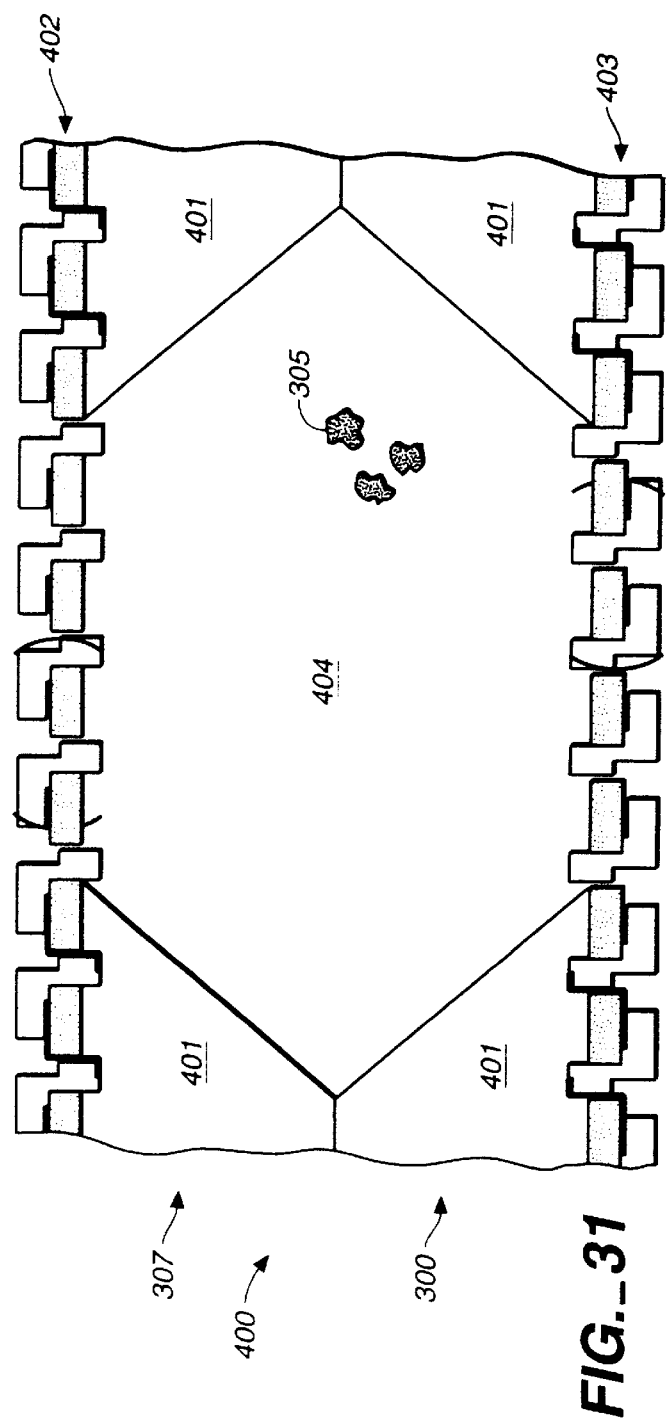

6,044,981

MICROFABRICATED FILTER WITH SPECIALLY CONSTRUCTED CHANNEL WALLS, AND CONTAINMENT WELL AND CAPSULE CONSTRUCTED WITH SUCH FILTERS

CROSS REFERENCE TO RELATED APPLICATIONS

This application is a divisional of U.S. application Ser. No. 08/663,644, filed Jun. 14, 1996, now Pat. No. 5,798,042, which is a continuation-in-part of U.S. patent application Ser. No. 08/482,237 filed Jun. 7, 1995, now Pat. No. 5,770,076, which is a continuation-in-part of U.S. patent application Ser. No. 08/254,330 filed Jun. 6, 1994, now Pat. No. 5,893,974, which is a continuation-in-part of U.S. application Ser. No. 08/207,457 filed Mar. 7, 1994, now Pat. No. 5,651,900 and a continuation-in-part of U.S. patent application Ser. No. 08/207,459 filed Mar. 7, 1994 now Pat. No. 5,660,680. The entire disclosures of these applications are incorporated herein by reference.

BACKGROUND OF THE INVENTION

The present invention relates generally to filtration devices and more particularly to microfabricated filters utilizing bulk substrate and thin film structures. The present invention further relates to biological containment wells and capsules for immunological isolation of cell transplants that are constructed with such filters.

Filtration devices are an indispensable necessity in the health care industry. Within the health care industry, accurate filtration devices are required, for example, in the fields of pharmaceutical technology, biotechnology, bioseparation, which includes plasma fractionation, and diagnostics. For many applications within these areas, required filtration device features include: precise control of pore sizes and distributions, absolute pore sizes as small as the nanometer (nm) range, mechanical strength, chemical inertness, high throughput, and high durability.

Filtration devices may, in particular, be utilized in containment wells and containment capsules constructed with such wells. Containment capsules are used for the immunological isolation of cell transplants. Containment wells may be used individually to evaluate the biological compatibility of different materials and to simulate the environment of containment capsules.

In a cell transplant, cells from a donor are transplanted into a host. The donor cells generate biologically-active molecules that provide the needed metabolic function in the host. As an example of a cell transplant, the islets of Langerhans, which produce insulin in mammals, have been transplanted between different species. However, unprotected islets function only for a short time before the immune system of the host kills the donor cells.

Encapsulation of islets in order to protect them from immune system macromolecules has been shown to prolong the survival of donor cells. For instance, by using various means of encapsulation, insulin production from pig islets has been maintained for over one hundred days in dogs. Encapsulation methods to date have used semipermeable amorphous organic polymeric membranes. Significant problems have been encountered, however, limiting the useful life of these capsules to not much more than one hundred days.

One problem with organic membrane capsules is inadequate mechanical strength. If the thickness of an organic membrane capsule wall is increased to provide the required mechanical strength, the biologically-active molecules cannot diffuse through the capsule wall quickly enough to provide the appropriate physiological response when needed.

Another problem with these capsules is insufficient control of pore size and pore distribution. If the size and distribution of pores cannot be controlled, such as with amorphous polymeric membranes, there is a high probability of oversized or overlapping pores which could provide an opening large enough for immunological macromolecules to enter the capsule.

Yet another problem with organic membrane capsules is their lack of biological compatibility and chemical inertness. The pores of the capsule membrane are susceptible to clogging by immunocytes, thus triggering an immune response in the host. The capsule membrane is also prone to adsorption of molecules such as proteins, causing the pores of the membrane to become clogged and thus restricting the passage of biologically-active molecules through the capsule wall. Furthermore, the capsule membrane is water soluble, thus limiting the capsule's useful life.

Precise control of filter pore sizes in the 5 to 20 nm range would allow biologically-important molecules to be mechanically separated on the basis of size. For instance, such pore sizes may be used to achieve the heretofore elusive goal of viral elimination from biological fluids. In the present state of the art, there is a very limited selection of filters having pore sizes much less than the resolution limit of photolithography, currently 0.35 micrometers ($\mu$m). The filters known heretofore having pore sizes in this range include polycarbonate membrane filters, sintered filters, zeolites, and microfabricated micromachined filters.

Polycarbonate membrane filters (nucleopore filters) may be used where pore sizes between 50 and 350 nm are needed. These filters, however, cannot be used at high temperatures, in strong organic solvents, or where no extracted oligomers can be tolerated. The pores of polycarbonate membrane filters are also randomly located. As such, there is a compromise between having a high enough population of pores per unit area and having too many instances of partially overlapping pores. Partially overlapping pores provide pathways through the filter that allow some particles to get through that are larger in diameter than the rated cut-off size of the filter.

Filters that are available in other materials, such as metals or ceramics, are made by sintering together discrete particles. This technique yields a random structure with a relatively large dead volume and no exact cut-off size above which transport is impossible.

Materials such as zeolites, which have a crystal structure with large channels, can be used as molecular sieves in the limited range of from about 0.5 nm to 5 nm. Zeolites are not amenable, however, to fabrication as thin membranes and thus provide a relatively low throughput.

A microfabricated filter comprised of surface micromachined structures is described in U.S. patent application Ser. No. 08/207,457, filed on Mar. 7, 1994, now U.S. Pat. No. 5,651,900, and assigned to the assignee of the subject application. The filter yields relatively uniform pore sizes and distributions. The pore sizes can be as small as about 5 nm. The walls of the filtration channels of the filter are entirely composed of polycrystalline silicon.

A microfabricated filter with a combination of surface and bulk micromachined structures is described by Kittilsland in Sensors and Actuators, A21–A23 (1990) pp. 904–907.

Unlike the previously described microfabricated filter, the filtration channels of this filter are partially composed of single crystalline silicon. Single crystalline silicon has an improved mechanical strength and chemical inertness over amorphous or polycrystalline silicon. As a result, the filter is relatively resistant to the adsorption of particles within a solution, such as protein molecules, that may clog its pores.

The pores of the filter described in Kittilsland are defined by diffusing regions of boron into the single crystalline silicon substrate through a silicon dioxide mask and then etching away the portions of the substrate that are not doped with boron. The length of the pores is determined by the extent of lateral diffusion of the boron through the substrate.

The filter of Kittilsland suffers from several disadvantages as a result of being fabricated by this process. First, the mechanical strength of the filter cannot be increased without increasing the length of the pores. This is because the thickness of the etched substrate and the length of the pores are both dependent on the diffusion of boron into the substrate and cannot be controlled independently of each other. Second, the pore length of the filter is not tightly controlled. This is because the rate of lateral diffusion of boron into the substrate, which affects the pore length, cannot be precisely regulated. Third, the fabrication process cannot be used to construct a filter with in-line pores, i.e., pores that have channels aligned in the same direction as the liquid flow. Fourth, the bulk micromachined structure of the filter has a non-uniform thickness, thus reducing the filter's mechanical strength. This results from the hemispherical shape of the regions of boron diffused into the substrate. Fifth, the density of pores in the filter is limited. This is again due to the use of regions of boron diffusion to define the pores.

An improved filter should combine mechanical strength with the ability to allow the free diffusion of small molecules such as oxygen, water, carbon dioxide, and glucose, while preventing the passage of larger molecules such as the immunoglobins and major histocompatibility (MHC) antigens. Furthermore, such a filter should allow the diffusion of intermediate sized molecular products, such as insulin, at a sufficient rate to enable a containment capsule utilizing such a filter to provide the needed metabolic function in the host. The filter should also be resistant to the adsorption of molecules. Finally, the filter should provide a high throughput or flow rate per unit area. A high throughput may be provided by constructing the filter out of a very thin membrane. Throughput may also be improved by utilizing in-line pores.

Containment capsules utilizing such filters would have a longer life than presently-available capsules, and eliminate the need for anti-rejection drugs by the simple strategy of physically isolating the transplanted cells so that no immunological reaction can take place. Cells from any source could then be implanted in any host. Tissue matching of donor to recipient would not be a concern.

The ideal filter material for such capsules would be biologically compatible and chemically inert with sufficient mechanical strength to form a very thin membrane having at least a region with uniformly sized and spaced holes that are just large enough to let the desired biologically-active molecular product through, while totally blocking the passage of all larger immunological molecules. Such a structure cannot be made from a polymer with an amorphous molecular structure, by sintering together particles, or by intermeshed ceramic needles.

Accordingly, it is an object of the present invention to provide a filter having a precisely controlled pore width, length and distribution.

It is another object of the present invention to provide a filter having a very short pore width and length, with the pore width in the nanometer range.

Yet another object of the present invention is to provide a filter having a relatively high throughput.

An additional object of the present invention is to provide a filter that is made of a biologically compatible, chemically inert material having a mechanical strength sufficient to form a very thin membrane.

A further object of the present invention is to provide methods for the construction of such a filter using relatively simple fabrication techniques.

Yet another object of the present invention is to provide a containment well or capsule constructed with such a filter to let a desired biologically-active molecular product through the well or capsule at a physiologically desirable rate, while blocking the passage of all larger immunological molecules, thus providing an immunological isolation of cell transplants contained therein.

It is another object of the present invention to provide methods for the construction of such a containment well or capsule using relatively simple fabrication techniques.

Still another object of the present invention is to provide methods for administering a biologically-active molecule to a host organism deficient in endogenous production of said biologically-active molecule using such a containment capsule.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to microfabricated filters utilizing a bulk substrate structure and a thin film structure which have openings therethrough. The openings are positioned such that the openings through the bulk substrate are partially blocked by the thin film structure and the openings through the thin film structure are partially blocked by the bulk substrate structure. The pores of the filter are formed by spaces between the bulk substrate structure and the thin film structure. The spaces are defined by a subsequently removed sacrificial layer that is deposited between the bulk substrate structure and the thin film structure.

The present invention is also directed to methods for constructing such filters utilizing surface and bulk micromachining. A bulk substrate is initially provided. Openings are then formed in a front surface of the bulk substrate. Next, a sacrificial layer is formed on at least part of the front surface of the bulk substrate. A thin film structure is then formed over the bulk substrate and sacrificial layer. Next, openings are formed through the thin film structure that expose a portion of the sacrificial layer. The backside of the bulk substrate is then etched through to the openings on the front surface of the bulk substrate to form a bulk substrate structure with openings that pass through the structure. Finally, the sacrificial layer is removed to form the pores of the filter.

The pores of the filter are of substantially uniform width, length and distribution. The width of the pores is defined by the thickness of the sacrificial layer and therefore may be smaller than the limit obtainable with photolithography. The pore width may be as small as about 15 nanometers (nm). The length of the pores may be determined by photolithography and may range from about 0.3 μm to many micrometers.

The filters provide enhanced mechanical strength, chemical inertness, biological compatibility, and throughput. The filters are suitable for use at high temperatures and pressures and with harsh solvents. The filters are relatively simple to fabricate, requiring, in one embodiment, only a single mask for the various photolithographic steps.

The present invention is further directed to microfabricated containment wells and containment capsules constructed with such filters for the immunological isolation of cell transplants, and methods for constructing such containment wells and capsules. The containment wells have a similar structure to the filters, utilizing the bulk substrate structure of the filters to form the side walls of the wells. The containment capsules are formed by hermetically sealing the open ends of two containment wells together. The containment wells and capsules are filled with a cell, tissue or pharmaceutical composition capable of producing a desired biologically-active molecular product. The pores of the well and capsule are large enough to let the desired molecular product through, while blocking the passage of all larger immunological molecules.

The containment wells and capsules provide enhanced biological compatibility and useful life. The containment wells and capsules are relatively simple to fabricate.

BRIEF DESCRIPTION OF THE DRAWINGS

The accompanying drawings, which are incorporated in and constitute a part of the specification, schematically illustrate a representative embodiment of the invention and, together with the general description given above and the detailed description of the representative embodiment given below, serve to explain the principles of the invention.

FIG. 1 is a perspective, cross-sectional view of a filter in accordance with the present invention.

FIG. 2 is a cross-sectional view of an enlarged portion of the filter of FIG. 1.

FIG. 3 is a cross-sectional view of a further enlarged portion (circled area of FIG. 2) of the filter of FIG. 1.

FIG. 4 is a cross-sectional view of a magnified portion of an alternative embodiment of a filter in accordance with the present invention.

FIG. 5 is a cross-sectional view of a containment well in accordance with the present invention.

FIG. 6 is a cross-sectional view of a containment capsule in accordance with the present invention.

FIGS. 7–18 are cross-sectional views illustrating steps in the fabrication of the filter of FIG. 1.

FIGS. 19–22 and 24–29 are cross-sectional views illustrating steps in the fabrication of the filter of FIG. 4.

FIG. 23 is an overhead view of the relative positions of a mask utilized in the fabrication of the filter of FIG. 4 at different steps of the process.

FIGS. 30–31 are cross-sectional views illustrating steps in the fabrication of the containment capsule of FIG. 6.

DESCRIPTION OF THE REPRESENTATIVE EMBODIMENTS

The present invention is directed to microfabricated filters, microfabricated containment wells and capsules constructed with such filters, and methods for their fabrication.

A filter 100 in accordance with the present invention is shown in FIGS. 1, 2 and 3. Filter 100 includes a bulk substrate structure 101 with openings 102 and ribs 109, and a thin film structure 103 with openings 104. Bulk substrate structure 101 may, for instance, be composed of single crystalline silicon. The dimensions of openings 102 and 104 are determined by the resolution limit of photolithography and are preferably 2 micrometers (μm) in length and width.

Thin film structure 103 is positioned relative to bulk substrate structure 101 such that openings 102 through bulk substrate structure 101 are partially blocked by thin film structure 103 and openings 104 through thin film structure 103 are partially blocked by bulk substrate structure 101 to form the channel walls of pores 105. The width of the pores, dimension W, is the diameter of the largest spherical particle that can pass through the pore. The pore width is determined by the thickness of a sacrificial layer (not shown) formed between bulk substrate structure 101 and thin film structure 103 that is subsequently removed. The pore width is preferably about 20 nm, but may range from about 5 nm to 5000 nm or more. The length of the pores, dimension L, is the shortest path through the pore. The pore length is determined by the spacing between openings 102 and openings 104 and is of dimensions permitted by the resolution limit of photolithography. The pore length is preferably 2 μm, but may range from about 0.35 μm to 3 μm or more. Openings 102 and openings 104 also form the pore entrances or exits of filter 100, depending on the direction of liquid flow.

Pores 105 are constructed with straight channel walls and a relatively short pore length to maximize the liquid throughput of the filter. The flow of liquid through the filter is indicated by arrows 108. The liquid flow may also occur in the direction opposite to that of arrows 108.

Filter 200, which is an alternative embodiment of the present invention, is shown in FIG. 4. Filter 200 is fabricated using a simplified version of the process used to fabricate filter 100, requiring only a single mask for performing the various photolithographic steps. Furthermore, filter 200 provides in-line pore channels, which are aligned in the same direction as that of the liquid flow, for improved throughput over filter 100. Filter 200 includes a bulk substrate structure 201 with openings 202 and ribs 209, and a thin film structure 203 with openings 204. Bulk substrate structure 201 may, for instance, be composed of single crystalline silicon. The dimensions of openings 202 and 204 are determined by the resolution limit of photolithography and are preferably 2 μm in length and width.

Thin film structure 203 is positioned relative to bulk substrate structure 201 such that openings 202 through bulk substrate structure 201 are partially blocked by thin film structure 203 and openings 204 through thin film structure 203 are partially blocked by bulk substrate structure 201 to form the channel walls of pores 205. The width of the pores, dimension $W_1$, is the diameter of the largest spherical particle that can pass through the pore. The pore width is determined by the thickness of a sacrificial layer (not shown) formed between bulk substrate structure 201 and thin film structure 203 that is subsequently removed. The pore width is preferably about 20 nm, but may range from about 5 nm to 5000 nm or more. The length of the pores, dimension $L_1$, is the shortest path through the pore. The pore length is determined by the distance between the bottom of openings 204 and the bottom surface of bulk substrate structure 201. The pore length is preferably 2 μm, but may range from about 0.35 μm to 3 μm or more. Openings 204 also form the pore entrances or exits of filter 200, depending on the direction of liquid flow.

Pores 205 are constructed with straight, in-line channel walls and a relatively short pore length to maximize the liquid throughput of the filter. The flow of liquid through the filter is indicated by arrow 208. The liquid flow may also occur in the direction opposite to that of arrow 208.

A microfabricated containment well in accordance with the present invention is shown in FIG. 5. Containment well 300 includes a side wall structure 301, an end face 302, a cavity 303, and an open end 304. Side wall structure 301 is composed of a bulk substrate, such as single crystalline silicon. End face 302 is positioned at one end of side wall structure 301 and is comprised of the structure of filters 100 or 200. Cavity 303 is bounded by side wall structure 301 and end face 302. Cavity 303 may be filled with a cell, tissue or pharmaceutical composition 305 capable of producing a desired biologically-active molecular product. For instance, the islets of Langerhans, which produce insulin in mammals may be placed in the cavity. Open end 304 is defined by the end of side wall structure 301 opposite end face 302.

A microfabricated containment capsule in accordance with the present invention is shown in FIG. 6. Containment capsule 400 includes side wall structure 401, end faces 402 and 403, and cavity 404. Side wall structure 401 is composed of a bulk substrate, such as single crystalline silicon. End faces 402 and 403 are respectively positioned at each end of side wall structure 401 and are each comprised of the structure of filters 100 or 200. Cavity 404 is bounded by side wall structure 401 and end faces 402 and 403. Cavity 404 may be filled with a cell, tissue or pharmaceutical composition 305, such as the islets of Langerhans, capable of producing a desired biologically-active molecular product.

Referring to FIG. 7, fabrication of filter 100 may begin with a planar bulk substrate 500 such as a single crystalline <100>-silicon wafer. Boron is diffused into the front surface of the bulk substrate to form a heavily boron doped etch-stop layer 501. For a silicon wafer, the etch-stop layer comprises a layer of p+ silicon. The depth of the etch-stop layer may range from about 3 $\mu$m to 10 $\mu$m or more. The etch-stop layer is used to make the substrate resistant to a subsequent backside etch step. Upon completing the fabrication steps, the etch-stop layer forms bulk substrate structure 101 of filter 100.

The temperature, pressure and duration of the diffusion process will determine the depth of etch-stop layer 501. For instance, the diffusion may be performed using a solid boron source at 1125° C. for 6 hours, forming an etch-stop layer 6 $\mu$m thick.

Next, a low-temperature, wet oxidation is performed on etch-stop layer 501. This step is performed to remove the borosilicate glass (BSG) from the etch-stop layer that is generated during the boron diffusion. Without this step, it would be very difficult to remove the BSG quickly and completely. The oxidation may be performed, for instance, at 950° C. for 30 minutes.

Referring to FIG. 8, openings 502 are then photolithographically defined and plasma etched into etch-stop layer 501. The openings are preferably square in shape, having, for instance, a length and width (dimension $W_2$) of 2 $\mu$m and a depth (dimension $D_2$) of at least 6 $\mu$m. The openings must be etched deep enough to pass all the way through the etch-stop layer into the undoped region of the substrate. The depth of the openings depends on the parameters of the etch process used. For instance, the etch may be performed with a chlorine plasma at a temperature of 40° C., a chamber pressure of 425 mTorr, a radio-frequency (RF) power of 275 Watts, and a gas flow rate of 180 sccm for 10 minutes. This process produces openings 502 that are about 7 $\mu$m deep. Openings 502 define openings 102 of filter 100.

Next, referring to FIG. 9, a phosphosilicate glass (PSG) layer 503 is deposited on etch-stop layer 501. The PSG layer fills openings 502 in the etch-stop layer, forming a smooth surface.

Referring to FIG. 10, PSG layer 503 is then selectively removed from etch-stop layer 501, leaving openings 502 filled with PSG. This step may be performed using photolithography.

Next, referring to FIG. 11, a sacrificial layer 504 is grown on etch-stop layer 501 using thermal oxidation. It should be noted that the sacrificial layer does not form on openings 502 within the etch-stop layer since they are filled with PSG. The sacrificial layer, which is removed in a subsequent fabrication step, defines pores 105 of the filter. More specifically, the thickness of the sacrificial layer defines the width of the pores.

The thickness of sacrificial layer 504 may be determined by varying the oxidation time, temperature, and gas composition. The thickness of the sacrificial layer may range from several tens of nanometers to several micrometers. The oxide may be formed, for instance, by dry oxidation at 950° C. for 40 minutes, producing a 20 nm thick layer of silicon dioxide on a silicon wafer. If a carefully controlled environment is used to perform the oxidation, the variation in the thickness of the sacrificial layer may be less than 5% over a 4-inch substrate.

Referring to FIG. 12, anchor points 505 are then photolithographically defined and etched in sacrificial layer 504. The anchor points are used to provide openings in the sacrificial layer to fasten a subsequently deposited thin film layer to etch-stop layer 501.

Next, referring to FIG. 13, a thin film layer 506 is deposited on sacrificial layer 504 using low-pressure chemical vapor deposition (LPCVD). The thin film layer also covers the PSG in openings 502. The deposition may be performed, for instance, using silane gas ($SiH_4$) at a temperature of 605° C. and a pressure of 300 milliTorr, forming a 3 $\mu$m-thick layer of polysilicon. Thin film layer 504 contacts etch-stop layer 501 through anchor points 505, thus anchoring the thin film layer to the etch-stop layer. The thin film layer is used to form thin film structure 103 of filter 100.

The processed substrate 500 is then cleaned and annealed, for instance, at 1000° C. in a nitrogen ($N_2$) environment for one hour.

Referring to FIG. 14, thin film layer 506 is then heavily boron doped using diffusion, forming, for instance, p+ polysilicon. The diffusion may be performed, for instance, using a solid boron source at 1125° C. for 6 hours. This step is performed to prevent possible damage to the thin film layer during a subsequently performed long substrate backside etch.

Next, a low-temperature, wet oxidation is performed on thin film layer 506. As with etch-stop layer 501, this step is performed to remove the borosilicate glass (BSG) from the thin film layer that is generated during the boron diffusion. The oxidation may be performed, for instance, at 950° C. for 30 minutes.

Referring to FIG. 15, openings 507 are then photolithographically defined and plasma etched through thin film layer 506. The openings are preferably square in shape, having a length and width (dimension $W_3$), for instance, of 2 $\mu$m. For instance, the etch may be performed with a chlorine plasma at a temperature of 40° C., a chamber pressure of 425 mTorr, an RF power of 275 Watts, and a gas flow rate of 180 sccm for 4 minutes. Openings 507 form openings 104 of filter 100.

Next, referring to FIG. 16, substrate 500 is cleaned and a passivation layer 508 is grown on thin film layer 506 by thermal oxidation. The passivation layer is used to protect the thin film layer from a subsequently performed long substrate backside etch. The oxidation process may occur, for instance, for 1 hour at 1000° C., producing a passivation layer 0.38 µm thick.

As also shown in FIG. 16, a PSG layer 509 is deposited on thin film layer 506 to further protect the thin film layer from the backside etch. The thickness of the PSG layer may, for instance, be 2 µm. A PSG layer 510 is also deposited, photolithographically defined and etched on the backside of substrate 500 to define etch windows that will be used in the following step.

Referring to FIG. 17, substrate 500 is then anisotropically etched. The anisotropic etch may be performed with, for instance, ethylenediamine-pyrocatechol (EDP) for 10 hours at 100° C. The anisotropic etch of the substrate will automatically stop at etch-stop layer 501 and at PSG layer 503 in openings 502, thereby protecting thin film layer 506 from being etched. The anisotropic etch does not penetrate passivation layer 508 or PSG layer 509, thereby further protecting the thin film layer from the etchant. The anisotropic etch also does not penetrate PSG layer 510, thereby forming ribs 109 of filter 100 in substrate 500. This step defines bulk substrate structure 101 of filter 100.

Finally, referring to FIGS. 17 and 18, sacrificial layer 504, passivation layer 508, and PSG layers 503, 509 and 510 are etched using, for instance, buffered hydrofluoric acid (HF). This step removes the sacrificial layer so as to form pores 105 of filter 100. The processed substrate is then rinsed in deionized water to remove residual acid from the substrate.

Referring to FIG. 19, fabrication of filter 200 may begin with a planar bulk substrate 600 such as a single crystalline <100>-silicon wafer. Boron is diffused into the front surface of the bulk substrate to form a heavily boron doped etch-stop layer 601. For a silicon wafer, the etch-stop layer comprises a layer of p+ silicon. The depth of the etch-stop layer may range from about 3 µm to 10 µm or more. The etch-stop layer is used to make the substrate resistant to a subsequent backside etch step. Upon completing the fabrication steps, the etch-stop layer forms bulk substrate structure 201 of filter 200.

The temperature, pressure and duration of the diffusion process will determine the depth of etch-stop layer 601. For instance, the diffusion may be performed using a solid boron source at 1125° C. for 6 hours, forming an etch-stop layer 6 µm thick.

Next, a low-temperature, wet oxidation is performed on etch-stop layer 601. This step is performed to remove the borosilicate glass (BSG) from the etch-stop layer that is generated during the boron diffusion. Without this step, it would be very difficult to remove the BSG quickly and completely. The oxidation may be performed, for instance, at 950° C. for 30 minutes.

Referring to FIG. 20, openings 602 are then photolithographically defined and plasma etched into etch-stop layer 601. The openings are preferably square in shape, having, for instance, a length and width (dimension $W_4$) of 2 µm and a depth (dimension $D_4$) of at least 6 µm. The openings must be etched deep enough to pass all the way through the etch-stop layer into the undoped region of the substrate. The depth of the openings, which is precisely controllable, depends on the parameters of the etch process used. For instance, the etch may be performed with a chlorine plasma at a temperature of 40° C., a chamber pressure of 425 mTorr, an RF power of 275 Watts, and a gas flow rate of 180 sccm for 10 minutes. This process produces openings 602 that are about 7 µm deep. The depth of openings 602 affects the length $L_1$ of pores 205. Openings 602 also define openings 204 of filter 200.

Next, referring to FIG. 21, a sacrificial layer 603 is grown on etch-stop layer 601 and in openings 602 using thermal oxidation. The sacrificial layer, which is removed in a subsequent fabrication step, defines pores 205 of the filter. More specifically, the thickness of the sacrificial layer defines the width of the pores.

The thickness of sacrificial layer 603 may be determined by varying the oxidation time, temperature, and gas composition. The thickness of the sacrificial layer may range from several tens of nanometers to several micrometers. The oxide may be formed, for instance, by dry oxidation at 950° C. for 40 minutes, producing a 20 nm thick layer of silicon dioxide on a silicon wafer. If a carefully controlled environment is used to perform the oxidation, the variation in the thickness of the sacrificial layer may be less than 5% over a 4-inch substrate.

Referring to FIG. 22, anchor points 604 are then photolithographically defined and etched in sacrificial layer 603. In this embodiment of the invention, the photolithography is performed using the same mask as that used to define and etch openings 602 in etch-stop layer 601. Referring to FIG. 23, mask 700 is shifted from the position used to define openings 602, as indicated by A, to position A' to define anchor points 604. The mask is shifted by a sufficient distance, for instance, about 1 µm, such that anchor points 604 only partially overlap openings 602. The anchor points are positioned in this manner so that the anchor points do not substantially obstruct pores 205 of the finished filter 200. The anchor points are used to provide openings in the sacrificial layer to fasten a subsequently deposited thin film layer to substrate 600 and etch-stop layer 601.

Next, referring to FIG. 24, a thin film layer 605 is deposited on sacrificial layer 603 using low-pressure chemical vapor deposition (LPCVD). The thin film layer also fills openings 602 in etch-stop layer 601. The deposition may be performed, for instance, using silane gas ($SiH_4$) at a temperature of 605° C. and a pressure of 300 milliTorr, forming a 3 µm-thick layer of polysilicon. Thin film layer 605 contacts substrate 600 and etch-stop layer 601 through anchor points 604, thus anchoring the thin film layer to the substrate and etch-stop layer. The thin film layer is used to form thin film structure 203 of filter 200.

The processed substrate 600 is then cleaned and annealed, for instance, at 1000° C. in a nitrogen ($N_2$) environment for one hour.

Referring to FIG. 25, thin film layer 605 is then heavily boron doped using diffusion, forming, for instance, a layer of p+ polysilicon. The diffusion may be performed, for instance, using a solid boron source at 1125° C. for 6 hours. This step is performed to prevent possible damage to the thin film layer during a subsequently performed long substrate backside etch.

Next, a low-temperature, wet oxidation is performed on thin film layer 605. As with etch-stop layer 601, this step is performed to remove the borosilicate glass (BSG) from the thin film layer that is generated during the boron diffusion. The oxidation may be performed, for instance, at 950° C. for 30 minutes.

Referring to FIG. 26, openings 606 are then photolithographically defined and plasma etched through thin film layer 605. The openings are preferably square in shape, having, for instance, a length and width (dimension $W_5$) of 2 μm and a depth (dimension $D_5$) of at least 6 μm. For instance, the etch may be performed with a chlorine plasma at a temperature of 40° C., a chamber pressure of 425 mTorr, an RF power of 275 Watts, and a gas flow rate of 180 sccm for 10 minutes. This process produces openings 606 that are about 7 μm deep.

The photolithography in this step is performed using the same mask as that used to define and etch openings 602 in etch-stop layer 601 and anchor points 604 in sacrificial layer 603. Referring to FIG. 23, mask 700 is shifted from the position used to define openings 602, as indicated by A, to position A" to define openings 606. The mask is shifted by a sufficient distance, for instance, about 1 μm, such that openings 606 are positioned to function as pore entrances or exits for pores 205 of filter 200.

Next, referring to FIG. 27, a PSG layer 607 is deposited on thin film layer 605. This step is performed to protect the thin film layer from a subsequently performed long substrate backside etch. The thickness of the PSG layer may, for instance, be 2 μm. A PSG layer 608 is also deposited, photolithographically defined and etched on the backside of substrate 600 to define etch windows that will used in the following step.

Referring to FIG. 28, substrate 600 is then anisotropically etched. The anisotropic etch may be performed with, for instance, ethylenediamine-pyrocatechol (EDP) for 10 hours at 100° C. The anisotropic etch of the substrate will automatically stop at etch-stop layer 601 and at sacrificial layer 603 and thin film layer 605 in openings 602. The anisotropic etch does not penetrate PSG layer 607, thereby protecting the top surface of thin film layer from the etchant. The anisotropic etch also does not penetrate PSG layer 608, thereby forming ribs 209 of filter 200 in substrate 600. This step defines bulk substrate structure 201 of filter 200.

Finally, referring to FIG. 29, sacrificial layer 603 and PSG layers 607 and 608 are etched using, for instance, buffered hydrofluoric acid (HF). This step removes the sacrificial layer so as to form pores 205 of filter 200. The processed substrate is then rinsed in deionized water to remove residual acid from the substrate.

Fabrication of containment well 300, as shown in FIG. 5, may be performed by a similar process to that of filters 100 or 200. The anisotropic etch of substrate 500, as shown in FIG. 17, defines side wall structure 301, end face 302, cavity 303 and open end 304 of containment well 300. Cavity 303 of the containment well may be filled with a cell, tissue or pharmaceutical composition 305 capable of producing a desired biologically-active molecular product. For instance, the islets of Langerhans, which produce insulin in mammals may be placed in the cavity.

Referring to FIG. 30, fabrication of containment capsule 400 may begin with a containment well 300 fabricated as previously described. Cavity 303 of the containment well may be filled with a cell, tissue or pharmaceutical composition 305, such as the islets of Langerhans, capable of producing a desired biologically-active molecular product.

As also shown in FIG. 30, an adhesive 306 capable of creating a hermetic seal is then applied to open end 304 of containment well 300. The adhesive may be, for instance, Dow Corning 734 silicone rubber glue, available from Dow Corning Corporation, Midland, Mich.

Finally, referring to FIG. 31, the open end of a containment well 307 is placed next to the open end of containment well 300 to form a hermetic seal between the two containment wells. The side wall structures of containment wells 300 and 307 are thereby joined to form side wall structure 401 of capsule 400. Capsule 400 may also be constructed by joining the open end of containment well 300 with a substrate, rather than with another containment well.

The present invention has been described in terms of a representative embodiment. The invention, however, is not limited to the embodiment depicted and described. Rather, the scope of the invention is defined by the appended claims.

What is claimed is:

1. A method for forming a microfabricated filter, comprising the steps of:

providing a bulk substrate having a first surface;

forming openings in said first surface of said bulk substrate;

forming a sacrificial layer over at least part of said first surface of said bulk substrate;

forming a thin film layer over at least part of said first surface of said bulk substrate and said sacrificial layer;

forming openings through said thin film layer, wherein said openings through said thin film layer expose a portion of said sacrificial layer and are positioned relative to said openings in said bulk substrate such that said openings in said bulk substrate are at least partially blocked by said thin film structure and said openings in said thin film structure are at least partially blocked by said bulk substrate;

etching a second surface of said bulk substrate opposite said first surface of said bulk substrate through to said openings in said first surface of said bulk substrate, wherein said etching forms openings through said bulk substrate; and removing said sacrificial layer.

2. The method of claim 1, wherein said method utilizes only a single photolithographic mask.

3. A method for forming a microfabricated filter, comprising the steps of:

providing a bulk substrate;

forming an etch-stop layer within a first surface of said bulk substrate;

forming openings in said etch-stop layer using a first predetermined etching process, said openings extending through said etch-stop layer into said bulk substrate;

forming a sacrificial layer over at least part of said etch-stop layer;

forming a thin film layer over at least part of said etch-stop layer and said sacrificial layer;

forming openings through said thin film layer using said first predetermined etching process, wherein said openings through said thin film layer expose a portion of said sacrificial layer and are positioned relative to said openings in said bulk substrate such that said openings in said bulk substrate are at least partially blocked by said thin film structure and said openings through thin film structure are at least partially blocked by said bulk substrate, and wherein said first predetermined etching process does not etch said bulk substrate, said etch-stop layer, said sacrificial layer, or said thin film layer;

etching a second surface of said bulk substrate opposite said first surface of said bulk substrate through to said etch-stop layer using a second predetermined etching process, wherein said etching forms openings through said bulk substrate and said second predetermined etching process does not etch said etch-stop layer, said sacrificial layer or said thin film layer; and removing said sacrificial layer using a third predetermined etching process, wherein said third predetermined etching process does not etch said bulk substrate, said etch-stop layer or said thin film layer.

4. The method of claim 3, wherein said bulk substrate comprises single crystalline silicon.

5. The method of claim 3, wherein said etch-stop layer comprises boron-doped single crystalline silicon.

6. The method of claim 3, wherein said sacrificial layer comprises silicon dioxide.

7. The method of claim 3, wherein said thin film layer comprises boron-doped polysilicon.

8. The method of claim 3, wherein said first predetermined etching process comprises a plasma etch.

9. The method of claim 3, wherein said second predetermined etching process comprises an anisotropic etch.

10. The method of claim 3, wherein said third predetermined etching process comprises a buffered hydrofluoric acid etch.

11. The method of claim 3, wherein said method utilizes only a single photolithographic mask.

12. A microfabricated containment well, comprising:
   a one-piece side wall structure comprising a bulk substrate, said side wall structure having an open end;
   an end face connected to said side wall structure opposite said open end, said end face comprising a microfabricated filter; and
   a cavity bounded by said side wall structure and said end face.

13. The microfabricated containment well of claim 12 further comprising a substance contained within said cavity.

14. A microfabricated containment capsule, comprising:
   a side wall structure comprising a one-piece bulk substrate;
   at least one end face connected to said side wall structure, said end face comprising a microfabricated filter; and
   a cavity bounded by said side wall structure and said at least one end face.

15. The microfabricated containment capsule of claim 14 further comprising a substance contained within said cavity.

16. A method for forming a microfabricated containment capsule, comprising the steps of:
   forming a microfabricated containment well, said containment well having an open-faced cavity;
   placing a substance into said cavity of said containment well;
   providing a substrate; and
   hermetically sealing a face of said substrate to said open end of said containment well.

17. The method of claim 16, wherein said hermetic sealing utilizes a silicone rubber glue.

18. The method of claim 16, wherein said substance is a cell, tissue or pharmaceutical composition capable of producing a desired biologically-active molecule.

19. A method for forming a microfabricated containment capsule, comprising the steps of:
   forming a first microfabricated containment well and a second microfabricated containment well, each said containment well having an open-faced cavity;
   placing a substance into said cavity of said first containment well; and
   hermetically sealing said open end of said first containment well to said open end of said second containment well.

20. The method of claim 19, wherein said hermetic sealing utilizes a silicone rubber glue.

21. The method of claim 19, wherein said substance is a cell, tissue or pharmaceutical composition capable of producing a desired biologically-active molecule.

22. A method for forming a microfabricated containment capsule, comprising the steps of:
   forming a first and a second microfabricated containment well, each said containment well having a cavity and an open end, each said containment well formed by the steps of:
      providing a bulk substrate having a first surface;
      forming openings in said first surface of said bulk substrate;
      forming a sacrificial layer over at least part of said first surface of said bulk substrate;
      forming a thin film layer over said first surface of said bulk substrate and said sacrificial layer;
      forming openings through said thin film layer, wherein said openings through said thin film layer expose a portion of said sacrificial layer and are positioned relative to said openings in said bulk substrate such that said openings in said bulk substrate are at least partially blocked by said thin film structure and said openings through said thin film structure are at least partially blocked by said bulk substrate;
      etching an area of a second surface of said bulk substrate opposite said first surface of said bulk substrate through to said openings in said first surface of said bulk substrate, wherein said etching forms openings through said bulk substrate; and
      removing said sacrificial layer;
   placing a substance into said cavity of said first containment well; and
   hermetically sealing said open end of said first containment well to said open end of said second containment well.

23. The method of claim 22, wherein said hermetic sealing utilizes a silicone rubber glue.

24. The method of claim 22, wherein said substance is a cell, tissue or pharmaceutical composition capable of producing a desired biologically-active molecule.

* * * * *